United States Patent [19]

Hofke et al.

[11] Patent Number: 4,623,793

[45] Date of Patent: Nov. 18, 1986

[54] DEVICE AND METHOD FOR DETERMINING SKIN TYPE

[75] Inventors: Fred Hofke, East Greenville, Pa.; Irwin Margolin, Ardsley, N.Y.

[73] Assignee: Revlon, Inc., New York, N.Y.

[21] Appl. No.: 472,547

[22] Filed: Mar. 7, 1983

[51] Int. Cl.⁴ .......................... G01J 1/00; A61B 10/00
[52] U.S. Cl. .................................... 250/341; 128/759; 250/252.1
[58] Field of Search ............ 250/341, 340, 301, 252.1, 250/573; 356/71, 416; 128/759

[56] References Cited

U.S. PATENT DOCUMENTS

| | | | |
|---|---|---|---|
| 3,241,431 | 3/1966 | Brutten et al. | 356/71 |
| 3,999,948 | 12/1976 | Deindoerfer et al. | 356/246 |
| 4,224,950 | 9/1980 | Bore et al. | 128/759 |
| 4,281,932 | 8/1981 | Young | 356/416 |
| 4,286,327 | 8/1981 | Rosenthal et al. | 364/498 |
| 4,358,679 | 11/1982 | Lipoma | 250/252.1 |

OTHER PUBLICATIONS

Willard, H., Merritt, L., and Dean, J., Instrumental Methods of Analysis, 1974, p. 74.

*Primary Examiner*—Carolyn E. Fields
*Assistant Examiner*—Richard Hanig

[57] ABSTRACT

A battery-powered device and method for determining the skin type of a living subject is disclosed in which an oil sample carried by a probe is subjected to the impingement of an essentially monochromatic light source of predetermined wavelength. The amount of light passing through the oil sample is detected and an output voltage proportional thereto is produced. This output voltage is amplified, integrated and then drives an LED display which indicates the skin type of the subject. Calibration means and a method for calibrating the device utilizing both an oil-free and oily probe are disclosed. The calibration means include both means for adjusting the bandwidth of the output of the amplifying circuit and gain control means for adjusting the output voltage of the amplifying circuit.

16 Claims, 2 Drawing Figures

DEVICE AND METHOD FOR DETERMINING SKIN TYPE

CROSS REFERENCE TO RELATED APPLICATIONS

This application is related to the following applications, each of which is assigned to the assignee of this application and each of which was filed concurrently herewith:

U.S. patent application Ser. No. 472,548, "Probe For Machine For Determining Skin Type"; and U.S. patent application Ser. No. 472,781, now abandoned in favor of Ser. No. 767,078, "Device and Method For Determining Skin Type".

BACKGROUND OF THE INVENTION

The present invention relates generally to apparatus and a method for determining the skin type of an individual, and more particularly, to electronic apparatus utilizing a light source which is transmitted through an oil sample taken from the skin of an individual.

As is well known in the cosmetics, dermatology and pharmaceutical fields, a film or deposit of natural oil is present on the skin surface of a person. The formation of this oil film and its deposition on the skin is governed by the sebaceous glands which become active at about the time of puberty and continue to increase in activity until the person reaches the early twenties. Thereafter, the sebaceous glands then slowly diminish in efficiency and thus, the degree of oiliness of the skin is lessened as the person ages. It is also generally known that aged skin is a drier skin, e.g., there is less oil content.

Skin type may be divided into three broad categories with respect to skin oil content: (1) normal; (2) oilier than normal; and (3) drier than normal. Specific skin care and make-up products are designed to conform and to perform their functions according to skin type.

To determine an individual's skin type, a dermatologist will generally visually observe the patient's skin and relate the condition to the patient's age. Dermatologists also examine the skin surface for shininess as well as ease of transference of skin oil to a glass slide or test paper. The presence or absence of selected pathologic findings, such as blackheads, redness, scaling and the location of same, also contribute to a reasonably accurate determination of skin type.

To date, however, no reliable instrumentation has been available which will provide a truly objective evaluation and determination of the skin type of an individual, either by physicians or lay persons, e.g., cosmetologists.

Conventional apparatus for measuring the amount of oil or sebum secreted by the skin of a living subject generally fall into two classes. One such class of device is described in U.S. Pat. No. 4,224,950, to Bore et al, wherein the change in transparency of a glass plate due to oil adhering thereto is measured. The other class of devices are those which typically use chemical analysis methods, such as diffusion, gas chromatography and, as disclosed by Tur et al, U.S. Pat. No. 3,906,933, electrostatically charged printing surfaces which obtain an imprint of the skin. However, the drawback of this second class of devices is that although they may be intended for use by unskilled personnel, an analytical evaluation must later be conducted by skilled personnel, which evaluation is both costly and time consuming.

The device described in U.S. Pat. No. 4,244,950 to Bore et al is a sebumeter which is intended to evaluate the activity of the sebaceous glands by means of a sample of the sebum secreted by the skin in the vicinity of the forehead. This device comprises a casing for holding a removable sample-holder which projects from the casing. A translucent element carried by the sample-holder can be applied to the forehead of the subject. A scale is located within the casing and carries at least one reference mark which, upon illumination of the translucent element by means of a self-contained light source, enables the user of the device to read, by observation of the reference mark, the amount of sebum deposited on the sample-holder.

While such a device may be useful for determining the amount of sebum on the skin surface of one individual, some difficulty and a great deal of inconvenience arises when the glass plate used therewith must be changed. In addition, the device disclosed therein is mechanical in nature and is subject to mechanical failure, particularly the calibrated compression spring which is secured to the sample-holder. Another drawback of the Bore et al device is that it requires a certain period of time during which the user of the device must observe the location of the reference mark in order to determine the amount of sebum present on an individual's skin. Finally, due to the size of the Bore et al device, it is subject to easily being damaged when used at cosmetic counters, either by being dropped onto the counter, or onto the floor around the counter, where it may be subjected to crushing by salespersons or customers.

When a device for determining skin type is to be utilized by untrained or unskilled personnel, such as cosmetic counter salespersons, it is necessary that means be provided within the device such that accurate readings can be easily obtained. This is especially true with electronic devices which may be sensitive to ambient light and/or temperature, line voltage variations, battery life, rough handling, variations in probe construction, etc. The present invention is therefore provided with a calibration circuit to insure that accurate readings are continuously obtained with the subject skin type determining device. The method of calibrating the disclosed device is simple, rapid and accurate and thus is ideally suited for use by untrained or unskilled users.

Another conventional but non-relevant device is shown in U.S. Pat. No. 3,241,431 to Brutten et al, and discloses method and apparatus for the measurement of fingerprint density by measuring the opacity of a strip of translucent material carrying a fingerprint. The method of calibrating this device is complex and time consuming and therefore susceptible to error.

In designing a useful skin type determining device, it is important to consider the environment in which the device will be used. Typically, cosmetic counters are located in department and specialty stores. The selling areas in these stores are generally open and are illuminated by fluorescent lighting. Thus, in order to successfully design a reliable skin type determining device which utilizes optical principles, care must be taken to minimize the effects of outside and ambient light on the optical measurements performed by the device. Thus, the present invention utilizes an infrared light source of approximately 920 nm. In addition, the detected light passing through the probe is integrated prior to calculating skin type, thus compensating for the known fact that oil on the skin surface of a person may not be homogenous over a small area of skin.

In a known light absorptivity device, U.S. Pat. No. 4,281,932, to Young, an LED light source is utilized in combination with a light sensing device to determine the quantity of light passing through a translucent medium. The reading is stored and then a second reading is made with a reference medium. The device indicates when the measured absorptivity is equal to the known absorptivity, and thereby the absorptivity of the measured medium is known. The only relevance of this device to the present invention is its use of an LED light source. Young does not disclose a specific reason for using an LED as a light source, and, in fact, also discloses the use of an incandescent light source. Furthermore, the device of Young is disclosed at col. 2, line 11 to embody a light-tight housing 10 in which either light source is mounted.

In the cosmetic field, it is desirable that customers receive prompt and accurate answers so that the greatest number of customers can be evaluated within any given time period thereby maximizing the sales of cosmetics to these customers. The instant device readily fulfills this need.

SUMMARY AND OBJECTS OF THE INVENTION

In view of the foregoing, it should be apparent that there still exists a need in the art for apparatus and method for reliably determining the amount of oil on the skin surface of a living individual in a simple and low cost manner and which may be readily used to easily determine the skin type of that individual. It is, therefore, a primary object of this invention to provide apparatus for accurately analyzing an individual's skin oil sample which is characterized by its ease of use and calibration.

More particularly, it is an object of this invention to provide a device for use by untrained or unskilled personnel for determining skin type which employs a probe for receiving a sample of oil from an individual's skin.

Still more particularly, it is an object of this invention to provide a method of and apparatus for accurately determining an individual's skin type by using light transmission measurement elements.

It is also an object of this invention to provide a method of and apparatus for determining the skin type of an individual utilizing light transmission measurement elements which is unaffected by outside and ambient light that may be present in the environment in which the invention is used.

It is another object of this invention to provide a method of and apparatus for determining the skin type of an individual utilizing light transmission measurement elements in which the detected light passing through the oil-carrying probe is integrated prior to calculating the skin type, in order to compensate for the non-homogeneous nature of the oil taken from the skin of the individual by the probe.

Another object of the present invention is to provide a method of and apparatus for determining an individual's skin type which is of rugged construction, is simple to use and which is low in cost to manufacture.

Still another object of the present invention is to provide a device for determining skin type which is portable and battery-powered so that it can be placed on a counter top and moved from place to place without wires, cords or the like.

Briefly described, these and other objects of the present invention are accomplished by providing a device which accepts a plastic probe containing an oil sample taken from the skin of an individual whose skin type is to be determined. An essentially monochromatic beam of light is transmitted through the probe which is received by a light receptor arranged on the opposite side of the probe. "Essentially monochromatic" is used herein to describe light which has a peak at a particular wavelength with the other components of the light falling off rapidly from this peak wavelength. Thus, practically, the light is monochromatic. The signal from the light receptor is amplified and integrated and then used to drive display means which indicate the skin type of the individual from which the oil sample was obtained. A plurality of LEDS are utilized as the display means and are driven by a like plurality of comparators which sequentially turn on an LED as the integrated voltage rises. A calibration circuit is provided with the device so that when a clean probe is employed the display will be calibrated at zero or minimum light transmission. Batteries are used to power the light source, the light receptor, and all processing and calibrating circuitry.

The method aspects of the present invention comprise the steps of detecting that portion of the impinging essentially monochromatic light which is transmitted through the probe, producing an output voltage proportional to the amount of the detected light, integrating this output voltage, comparing the integrated voltage to a known reference voltage and displaying the result of this comparison to indicate the skin type of the subject being tested.

DETAILED DESCRIPTION OF THE PREFERRED EMBODIMENT

Figure 1:
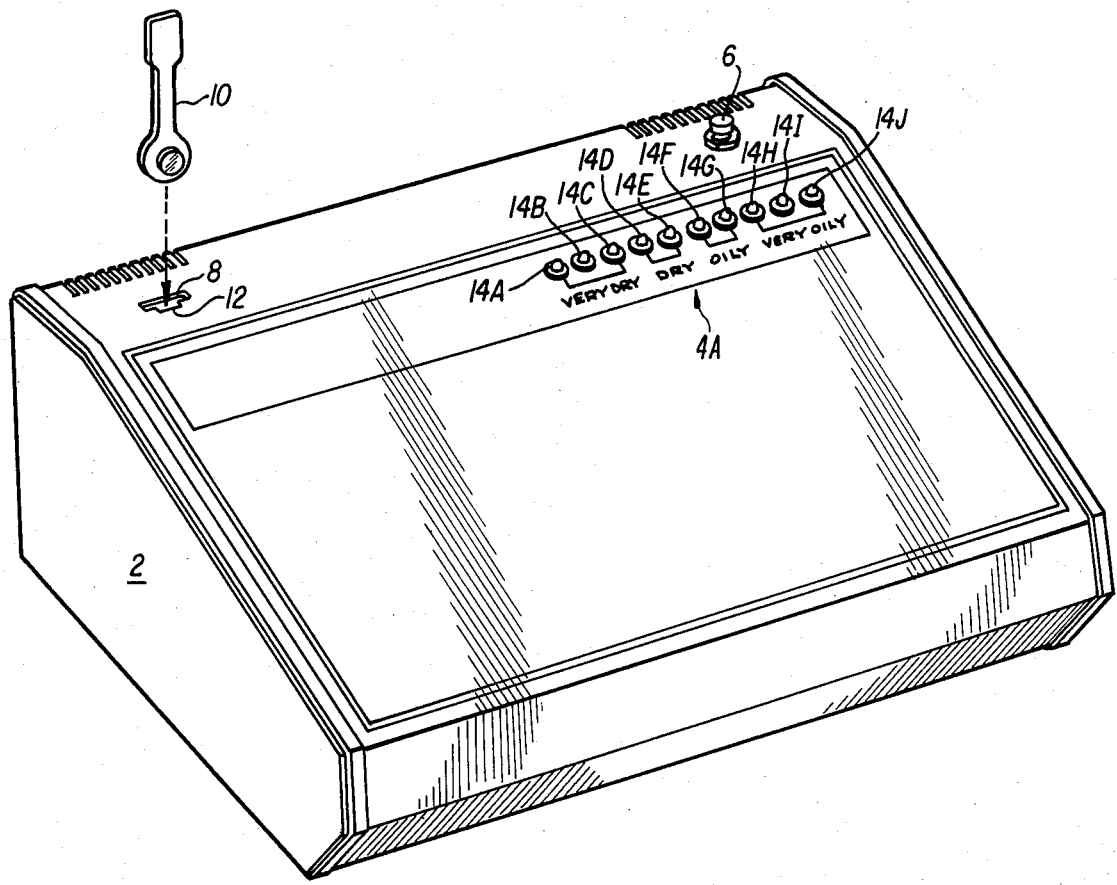
FIG. 1 is a perspective view showing the device for determining skin type of the present invention.

Referring now in detail to the drawings wherein like parts are designated by like reference numerals throughout, there is illustrated in FIG. 1 a housing 2 into which the various components of the inventive device are positioned for determining skin type. A record power switch 6A is provided on the front face of the case 2 for applying power to the circuitry.

A slot 8A is also provided on the front face of the case 2 for receiving a removable probe 10 which carries the oil sample from the skin of the individual being evaluated. The slot 8A includes a key 12 which insures that the probe 10 is inserted into the slot 8A with the correct orientation. Probe 10 is preferably made of plastic and of the type as more fully described in commonly assigned co-pending application Ser. No. 472,548, filed concurrently herewith entitled "Probe For Device For Determining Skin Type", the subject matter of which is incorporated herein by reference.

A scale 4 comprised of a plurality of LEDS 14A-J is provided on the front face of the case 2 for displaying the determined skin type. The circuitry of the instant skin type determining device is calibrated such that the scale 4 reads "oily" at one end to "dry" at the other end of the scale by lighting one of the plurality of diodes 14.

A calibration control 16 (not shown in FIG. 1) and a light receptor control 18 (not shown in FIG. 1) may be provided on the rear of the case 2. Once set, it is not usually necessary for the operator of the device to adjust the output range of the light receptor. Since these controls 16 and 18 are potentiometers, any suitable means of adjustment, such as knobs or slotted shafts may be provided to enable calibration of the device. A two terminal test point TP1 (not shown in FIG. 1) may also be provided for measuring a predetermined voltage present in the circuitry during calibration.

Figure 2:
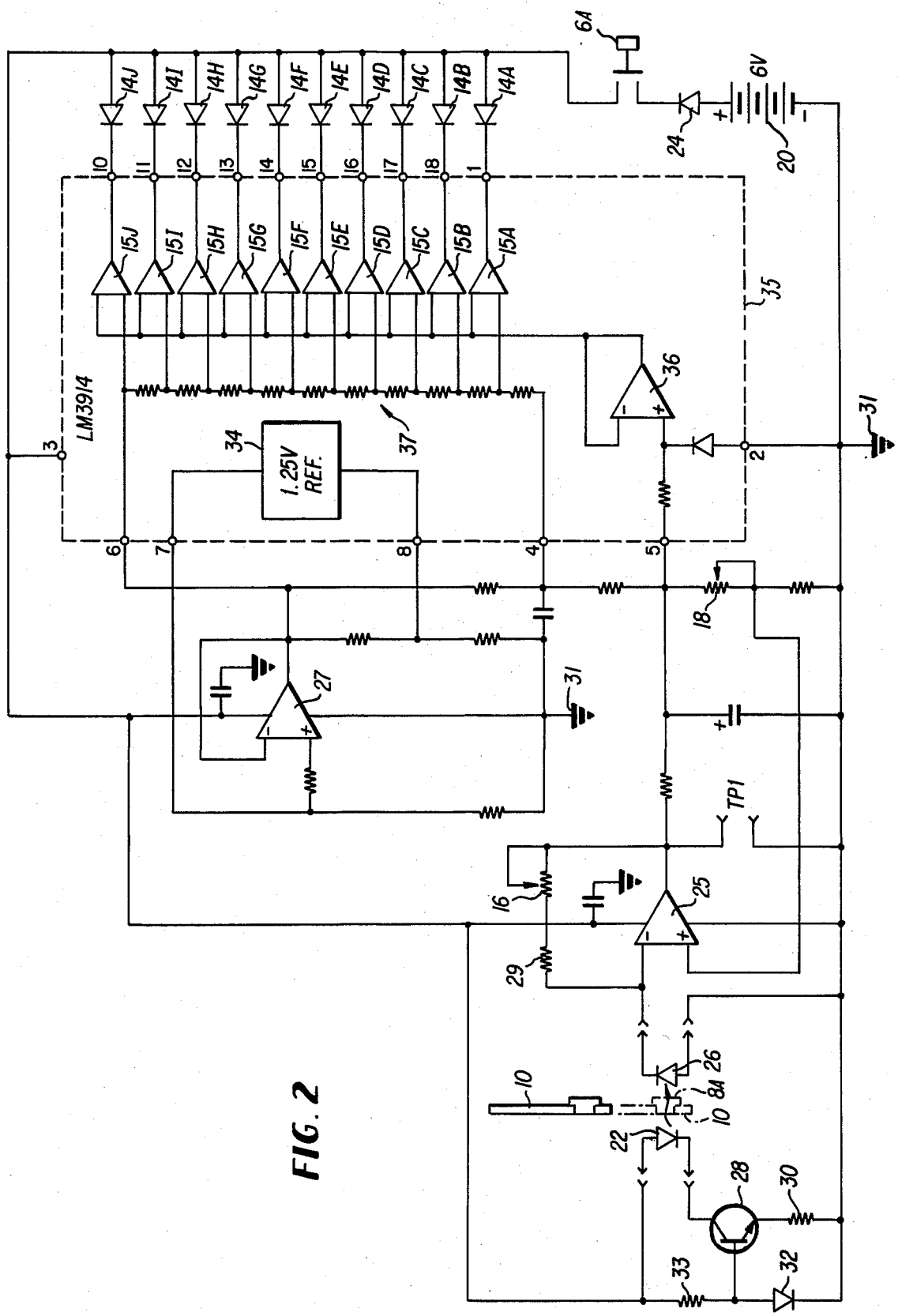
FIG. 2 is a schematic diagram of the circuitry of the present invention.

FIG. 2 shows the electrical schematic diagram of the instant device for determining skin type. Four 1.5 volt batteries 20 are utilized to power all circuits. As shown, one terminal of the record power switch 6A is connected through the positive terminal of a diode 24 to the positive terminal of the batteries 20. The other terminal of the single-pole momentary contact switch 6A is connected to power the circuitry of the instant device.

In particular, this other terminal of the power switch 6A is connected to the negative terminal of an infrared light emitting diode 22 which may preferably emit light with a peak wavelength of 920 nanometers or 9200 Å. This light passes through the lens of the probe 10 which has been inserted into place in the slot 8 and is received by a light receptor 26. This light receptor may preferably be a photovoltaic light sensor, such as a solar cell of 3 mm×3mm dimensions and an output of approximately 0.45 A/W. Of course, other suitable light receptors may be utilized.

The positive terminal of the diode 22 is connected to the collector of a transistor 28 which may be a 2N3646 type. This transistor 28 has its emitter connected through a resistor 30 to the negative pole of the battery, which operates at ground level, and has its base connected to the negative terminal of a diode 32 whose positive terminal is also connected to the common ground 31. A resistor 33 is connected between the base of the transistor 28 and the negative terminal of the IR LED 22. In this configuration, the input voltage to the IR LED 22 is voltage controlled by the transistor 28 such that the intensity of the IR light beam emitted by diode 22 essentially does not vary.

It should be understood that the light emitting diode 22 may emit light in the green, yellow, red or infrared spectra, although it has been found that infrared light of approximately 920 nm produces good operational results which eliminate the effects of spurious and background light caused by electric lights in the vicinity of operation of the instant device. Furthermore, the use of a light emitting diode and accompanying microcircuitry results in a very small battery drain such that the shelf life of the batteries 20 becomes the limiting factor for battery replacement, rather than the drain on the batteries due to the operation of the device.

The output from the light receptor 26 is fed, via its positive terminal, to an amplifier 25 which may preferably be an IC, such as a CA 3130T, manufactured, for instance, by Sylvania, RCA, Texas Instruments, and others. The output voltage of the light receptor 26 varies with the intensity of the light received from the IR LED 22 passing through the lens of the probe 10, from the frosted side thereof. The amount of light transmitted through the lens thus varies according to the amount of oil on the lens. The output of the light receptor is amplified by the amplifier 25 to a range useful by the remainder of the circuitry of the instant skin typing device. A second IC amplifier 27, which may also be a CA 3130T, is also utilized, as will be described hereinafter.

Each of the IC amplifiers 25 and 27 are connected at pins 7 thereof through the power switch 6 to the positive source of potential from the batteries 20 and at pin 4 to a negative potential source on common ground 31. The cathode of light receptor 26 is connected to pin 2 of IC amplifier 25 while its anode is connected to ground 31. The test points TP1 are connected between the output pin 6 of IC amplifier 25 and ground 31. These test points will be discussed in more detail hereinafter.

Input pin 2 of the amplifier 25 is connected through a resistor 29 to one terminal of the calibration control or potentiometer 16. The other terminal of the potentiometer 16, as well as its wiper, are connected to the output of the amplifier 25, in order to control the output voltage of this amplifier 25 and thus the gain of the amplified light sensor 26 signal.

Input pin 3 of the amplifier 25 is connected to the wiper of the light receptor range control or potentiometer 18. This potentiometer is connected between ground 31 and the output of the amplifier 27 and serves to control the spread of the amplified output voltage of the light receptor 26 in order to adjust the circuitry of the skin typing device to indicate the desired detected range of skin types. The voltage utilized to operate the plurality of LEDs 14A-J may typically be 0.5 volts.

The output from the amplifier 25 is applied to an integrated circuit 35, which may be a No. LM 3914, which contains a voltage divider 37, ten comparators 15A-J and a 1.25 reference voltage source 34. The ten comparators 15A-J turn on in sequence as the voltage supplied to them increases. Since each of the comparators 15A-J is connected to illuminate a separate one of the plurality of LEDs 14A-J, each connected by its cathode to the output of its respective comparator 15 and by its anode to a source of positive potential, the appropriate LED 14A-J will be illuminated to indicate the skin type of the subject individual under test.

The output from the amplifier 25 is fed to an integrator 36 contained on the IC 35. The output from the integrator 36 is applied to one input of each of the plurality of comparators 15. The second IC amplifier 27 is connected to the output of the IC 35 and is used to amplify this output voltage. The output of the amplifier 27 is connected to pin 6 of the IC 35 and consequently the other input to each of the plurality of comparators 15.

In operation, after the device has been calibrated as described hereinafter, the device operates as follows to determine an individual's skin type. A clean probe is pressed by the salesperson to the skin of the individual, for example, behind the ear. At this time, an oil sample is picked up by the probe 10. This oil sample-containing probe 10 results in a probe which is then inserted into the slot 8A and the record switch 6A, which may be a momentary-contact push button switch, is depressed. This activates the infrared light emitting diode 22 which emits a narrow light beam which passes through the oil sample contained on the lens of the probe 10. The light receptor or solar cell 26 detects the amount of light transmitted through this lens containing the oil sample and produces an output voltage proportional thereto. Since the oil sample on the probe 10 offers less resistance to the light transmitted therethrough than a clean or oil-free probe, the voltage output of the solar cell 26 will increase, and will cause a higher numbered LED 14A-J to be illuminated. This would indicate an oilier skin condition.

Thus, the output from the solar cell 26 is fed through the amplifier 25 to the integrator 36 contained in the integrated circuit 35. The output of the integrator 36 is connected to one input of each of the comparators 15 while the output of the second IC amplifier 27 is connected to the other input of each of the comparators. Upon the desired correspondence of voltages, the output from one of the comparators 15A-J then illuminates one of the LED's 14A-J, marked on the case 2 to indicate an oily condition from "very dry" to "very oily", thus indicating the skin type of the tested individual.

If desired, the record power switch 6A could be directly actuated by the insertion of the probe 10 in the slot 8A instead of by means of a separate switch.

The calibration procedure is as follows: The bandwidth potentiometer 18 is placed at approximately its midpoint in value and a probe 10 having a very oily lens is inserted into the slot 8A. The gain potentiometer 16 is then rotated in a clockwise direction until light emitting diode 14J is illuminated. A probe 10 having a clean lens is then inserted in slot 8A in place of the probe 10 with an oily lens. If no LED 14A-J is illuminated then the voltage at TP1 is below that at pin 4 of the integrated circuit 35, indicating that the range of the detector signal is too great for the IC 35.

Thus, the potentiometer 18 must be backed off, or rotated counter-clockwise, until LED 14A is illuminated. Once LED 14A is illuminated, the probe 10 with a clean lens is removed and the probe 10 with the oily lens again inserted into the slot 8A. The gain potentiometer 16 is again adjusted until LED 14J is illuminated. The probe 10 with the oily lens is then replaced by the probe 10 with the clean lens and the potentiometer 18 is rotated so that LED 14A is illuminated. The skin type determining device is then calibrated and ready for use.

It is contemplated that both the gain control 16 and the potentiometer 18 may be adjusted at the place of manufacture and thus it should not ordinarily be necessary for a salesperson to calibrate the instant skin type determining device.

Although only a preferred embodiment is specifically illustrated and described herein, it will be appreciated that many other modifications and variations of the present invention are possible in light of the above teachings and within the purview of the appended claims without departing from the spirit and intended scope of the invention.

What is claimed is:

1. A device means for determining the skin type of a living subject utilizing an oil sample taken from the skin of the subject and held on a probe capable of permitting light to pass therethrough, comprising:
    means for impinging essentially monochromatic light on one side of said probe;
    means for detecting that portion of the impinging light which is transmitted through said oil sample carried by said probe, said detecting means producing an output voltage proportional to the amount of light detected;
    means for integrating said output voltage; and voltage for displaying the skin type of said living subject as a function of said integrated output voltage wherein said means for detecting includes amplifying means connected to receive said output voltage from said means for detecting and said essentially monochromatic light is infrared light.

2. The device means of claim 1, further including slot means for receiving said probe, said means for impinging essentially monochromatic light and said means for detecting being located on opposite sides of said slot.

3. The device means of claim 1, wherein said essentially monochromatic light is infrared light of about 920 nanometers.

4. The device means of claim 1, wherein said means for displaying comprises voltage divider and comparator means connected to receive the integrated voltage and light emitting means which are selectively illuminated by said comparator means to display the skin type of the living subject.

5. The device means of claim 4, further including calibration means connected such that the means for displaying can be adjusted to display a predetermined reading when a probe without an oil sample thereon is utilized in place of an oil sample containing probe.

6. The device means of claim 1, wherein said light detecting means is positioned on the side of said probe opposite said impinging light means.

7. The device means of claim 4, further including adjusting means for said means for detecting, connected to said amplifying means such that the output of said amplifying means can be adjusted, in accordance with the operational characteristics of said means for detecting, to produce a range at least equal to the voltage range of the display means.

8. The device means of claim 3, wherein said means for detecting includes amplifying means connected to receive said output voltage from said means for detecting.

9. The device means of claim 8, further including calibration means connected such that the means for displaying can be adjusted to display a predetermined reading when a probe without an oil sample thereon is utilized in place of an oil sample containing probe.

10. The device means of claim 9, further including bandwidth adjusting means for said means for detecting, connected to said amplifying means such that the output of said amplifying means can be adjusted, in accordance to the operational characteristics of said means for detecting, to produce a bandwidth equal to the voltage range of the display means.

11. The device means of claim 1, wherein said means for displaying comprises voltage divider and comparator means connected to receive the integrated output voltage and light emitting means which are selectively illuminated by said comparator means to display the skin type of the living subject.

12. A method of calibrating a device for determining the skin type of a living subject, which device utilizes an oil sample taken from the skin of the subject and held on a probe capable of permitting light to pass therethrough, comprising the steps of:
    impinging essentially monochromatic light comprising infrared light on one side of a probe which is free of oil;
    detecting that portion of said impinging essentially monochromatic light which is transmitted through said probe;
    producing an output voltage proportional to the amount of the detected light;
    amplifying said output voltage;
    integrating said amplified output voltage and applying the integrated amplified signal to display means; and
    adjusting the amplification of said output voltage to produce a predetermined desired reading on said display means.

13. The method of claim 12, further including the step of adjusting the bandwidth of said amplified signal to coincide with the bandwidth of said display means.

14. The method of claim 12, wherein said essentially monochromatic light is infrared light having a wavelength of about 920 nanometers.

15. A method for determining the skin type of a living subject, which device utilizes an oil sample taken from the skin of the subject and held on a probe capable of permitting light to pass therethrough, comprising the steps of:

obtaining an oil sample taken from the skin of the subject on a probe;

impinging essentially monochromatic light comprising infrared light on one side of a probe;

detecting that portion of said impinging essentially monochromatic light which is transmitted through said probe;

producing an output voltage proportional to the amount of the detected light;

integrating said output voltage; and displaying said integrated output voltage to indicate the type of skin of the subject being tested.

16. The method of claim 15, wherein said essentially monochromatic light is infrared light of about 920 nanometers.

* * * * *